United States Patent
Valdez et al.

(10) Patent No.: US 12,121,220 B2
(45) Date of Patent: Oct. 22, 2024

(54) OPTICAL SYSTEMS AND METHODS FOR INTRAOPERATIVE DETECTION OF CSF LEAKS

(71) Applicants: THE BOARD OF TRUSTEES OF THE LELAND STANFORD JUNIOR UNIVERSITY, Stanford, CA (US); Helmholtz Zentrum Muenchen-Deutsches Forschungszentrum fur Gesundheit und Umwelt (GmbH), Neuherberg (DE)

(72) Inventors: Tulio A. Valdez, Palo Alto, CA (US); Mahbuba Tusty, Panorama City, CA (US); David Huland, San Francisco, CA (US); Oliver Bruns, Neuherberg (DE)

(73) Assignee: The Board of Trustees of the Leland Stanford, Jr. University, Stanford, CA (US)

( * ) Notice: Subject to any disclaimer, the term of this patent is extended or adjusted under 35 U.S.C. 154(b) by 365 days.

(21) Appl. No.: 17/543,365

(22) Filed: Dec. 6, 2021

(65) Prior Publication Data

US 2022/0087592 A1 Mar. 24, 2022

Related U.S. Application Data

(63) Continuation of application No. PCT/US2020/036527, filed on Jun. 7, 2020.
(Continued)

(51) Int. Cl.
*A61B 1/06* (2006.01)
*A61B 1/00* (2006.01)
(Continued)

(52) U.S. Cl.
CPC ........ *A61B 1/0638* (2013.01); *A61B 1/00045* (2013.01); *A61B 1/043* (2013.01);
(Continued)

(58) Field of Classification Search
CPC ... A61B 1/0638; A61B 1/00045; A61B 1/043; A61B 1/044; A61B 1/046; A61B 1/063;
(Continued)

(56) References Cited

U.S. PATENT DOCUMENTS 6,602,186 B1 * 8/2003 Sugimoto .......... G02B 23/2484
600/478
2017/0020377 A1 * 1/2017 Takeuchi ............... A61B 1/043
(Continued)

OTHER PUBLICATIONS

Carr, Jessica A., et al. "Shortwave infrared fluorescence imaging with the clinically approved near-infrared dye indocyanine green." Proceedings of the National Academy of Sciences 115.17 (2018): 4465-4470. (Year: 2018).*
(Continued)

*Primary Examiner* — Sean D Mattson
(74) *Attorney, Agent, or Firm* — William A. English; Vista IP Law Group LLP

(57) ABSTRACT

A multi-wavelength surgical system is provided using an endoscope sensitive in the short-wave infrared region which allows exploration of different areas of the skull base for CSF leaks. The device includes an LED box with multiple wavelengths including allowing excitation of ICG with 785-808 nm, enhancing the water absorption from 1200-1550 nm and above 1800 nm and incorporating white light to allow for surgical navigation. Because CSF is 99% water having a large absorption in the SWIR band around 1200-1550 nm and above 1800 nm, the system and method should be an effective means of diagnosis without the need for intrathecal fluorescein.

20 Claims, 3 Drawing Sheets

Related U.S. Application Data

(60) Provisional application No. 62/858,934, filed on Jun. 7, 2019.

(51) Int. Cl.
*A61B 1/04* (2006.01)
*A61B 1/233* (2006.01)
*A61B 5/00* (2006.01)

(52) U.S. Cl.
CPC .............. *A61B 1/044* (2022.02); *A61B 1/046* (2022.02); *A61B 1/063* (2013.01); *A61B 1/0684* (2013.01); *A61B 1/233* (2013.01); *A61B 5/0071* (2013.01); *A61B 5/4058* (2013.01)

(58) Field of Classification Search
CPC ..... A61B 1/0684; A61B 1/233; A61B 5/0071; A61B 5/4058; A61B 5/032; A61B 5/6819; A61B 90/30; A61B 2090/306; A61B 2090/3614; A61K 49/0034
See application file for complete search history.

(56) References Cited

U.S. PATENT DOCUMENTS

2018/0279864 A1* 10/2018 Frangioni ............ A61B 5/0071
2020/0337542 A1* 10/2020 Stewart .................... A61B 1/07

OTHER PUBLICATIONS

Horosh, Michael, et al. "Broadband infrared spectroscopy for non-contact measurement of neurological disease biomarkers in cerebrospinal fluid." Applied Spectroscopy 71.3 (2017): 496-506. (Year: 2017).*

* cited by examiner

OPTICAL SYSTEMS AND METHODS FOR INTRAOPERATIVE DETECTION OF CSF LEAKS

RELATED APPLICATION DATA

The present application is a continuation of co-pending International Application No. PCT/US2020/036527, filed Jun. 7, 2020, which claims benefit of U.S. provisional application Ser. No. 62/858,934, filed Jun. 7, 2019, the entire disclosures of which are expressly incorporated by reference herein.

FIELD OF THE INVENTION

The present invention relates to apparatus, systems, and methods for detecting cerebrospinal fluid ("CSF") leaks.

BACKGROUND

CSF leaks are a potential complication of endoscopic skull base surgery (Lee, 2008). In recent years, endoscopic skull base surgery has undergone significant advancements, leading to its increased use (Karnezis, 2016). Other causes of CSF leaks also include cranial trauma, skull base tumors, calcifications penetrating the dura, and genetic disorders of connective tissue in addition to spontaneous CSF leaks (Schievink, 2004). However, CSF leaks from endonasal skull base surgery remain the most common iatrogenic cause. In one study, as high as 30.1% of patients had an intraoperative CSF leak post endoscopic sellar surgery (Karnezis, 2016).

Current methods of intraoperative CSF leak diagnosis involve the off-label use of intrathecal fluorescein injections and subsequent visualization using nasal endoscopy or testing for the CSF specific compound Beta-2 transferrin (Lobo, 2017). However, despite their clinical usefulness, both methods have drawbacks. Fluorescein has not yet been approved for intrathecal injection due to its rare, but serious side effects including paraparesis, numbness, and seizure which are frequently reported to be associated with intrathecal use of fluorescein (Raza, 2015).

Moreover, a lack of intraoperative fluorescein visualization may not successfully rule out the presence of CSF leak, as evidenced by a false-negative rate of 26.2 percent in some studies (Seth, 2010). Furthermore, testing for Beta-2 transferrin requires adequate collectable CSF rhinorrhea to be present and is not an immediate diagnostic tool (Haft, 2004). Hence, accurate intraoperative localization of CSF leaks remain a potentially challenging task, even for experienced sinus surgeons (Seth, 2010). However, if CSF leaks are not caught and attenuated in a timely fashion, they can impact a surgeons closure technique and cause issues down the line for the patient including meningitis and headaches.

Accordingly, apparatus and methods for detecting CSF leaks would be useful.

SUMMARY

The present invention is directed to apparatus, systems, and methods for detecting cerebrospinal fluid ("CSF") leaks.

A multi-wavelength surgical apparatus and system are provided using an endoscope sensitive in the short-wave infrared region, which allows exploration of different areas of the skull base for CSF leaks. In an exemplary embodiment, the device includes an LED box with multiple wavelengths including allowing excitation of indocyanine green ("ICG") with 785-808 nm, enhancing the water absorption from 1200-2500 nm and incorporating white light to allow for surgical navigation. Because CSF is 99% water having a large absorption in the short wavelength infrared ("SWIR") band, e.g., around 1200-2500 nm, the apparatus and systems herein may be an effective means of diagnosis without the need for intrathecal fluorescein.

In accordance with an exemplary embodiment, an apparatus is provided for detecting leakage of cerebrospinal fluid in a subject's body that includes an imaging device comprising a proximal end, a distal end sized for introduction into the body, and an imaging element carried by the distal end; a light source coupled to the imaging device to simultaneously deliver near infrared (IR) light to excite fluorescent dye administered to the body to cause the dye to fluoresce and deliver short wavelength infrared (SWIR) light; and a camera for acquiring images via the imaging element within the SWIR band to facilitate identifying a leak of cerebrospinal fluid.

In accordance with another embodiment, a system is provided for detecting leakage of cerebrospinal fluid in a subject's body that includes an imaging device comprising a proximal end, a distal end sized for introduction into the body, and an imaging element carried by the distal end; a light source coupled to the imaging device to simultaneously deliver near infrared (IR) light to excite fluorescent dye administered to the body to cause the dye to fluoresce and deliver short wavelength infrared (SWIR) light; a camera for acquiring images via the imaging element within the SWIR band to facilitate identifying a leak of cerebrospinal fluid; and a source of fluorescent dye for administration to the subject.

In accordance with yet another embodiment, an apparatus is provided for detecting leakage of cerebrospinal fluid in a subject's body that includes an imaging device comprising a proximal end, a distal end sized for introduction into the body, and an imaging element carried by the distal end; a light source coupled to the imaging device comprising a source of near infrared (IR) light, a source of short wavelength infrared (SWIR) light, and a source of visible light; a camera for acquiring images via the imaging element within the SWIR band to facilitate identifying a leak of cerebrospinal fluid; and one or more actuators coupled to the light source for a) simultaneously activating the near IR light source and the SWIR light source while the visible light source is deactivated to excite fluorescent dye administered to the body to cause the dye to fluoresce and deliver SWIR light such that the images facilitate identifying a leak of cerebrospinal fluid, and b) activate the visible light source such that the camera acquires visible light images to facilitate navigation of the distal end within the body.

In accordance with still another embodiment, a method is provided for detecting leakage of cerebrospinal fluid in a subject's body that includes administering fluorescent dye to the body; introducing an imaging device into a target location within the body; delivering near infrared light via the imaging device to excite the fluorescent dye to cause the dye to fluoresce; and acquiring images via the imaging device at a frequency between about 1200-2500 nm to identify a leak of cerebrospinal fluid within the target location.

In accordance with another embodiment, an apparatus is provided for detecting leakage of cerebrospinal fluid in a subject's body that includes an imaging device comprising a proximal end, a distal end sized for introduction into the body, and an imaging element carried by the distal end; a light source coupled to the imaging device to deliver short wavelength infrared (SWIR) light; and a camera for acquiring images via the imaging element within the SWIR band to facilitate identifying a leak of cerebrospinal fluid based on contrast of the fluid provided by the SWIR light.

In accordance with still another embodiment, a method is provided for detecting leakage of cerebrospinal fluid in a subject's body that includes introducing a distal end of an imaging device into a target location within the body; delivering, from the distal end into the target location, short wavelength infrared (SWIR) light; and acquiring images via the imaging device at a frequency between about 1200-2500 nm to identify a leak of cerebrospinal fluid within the target location based upon contrast of the fluid provided by the SWIR light.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
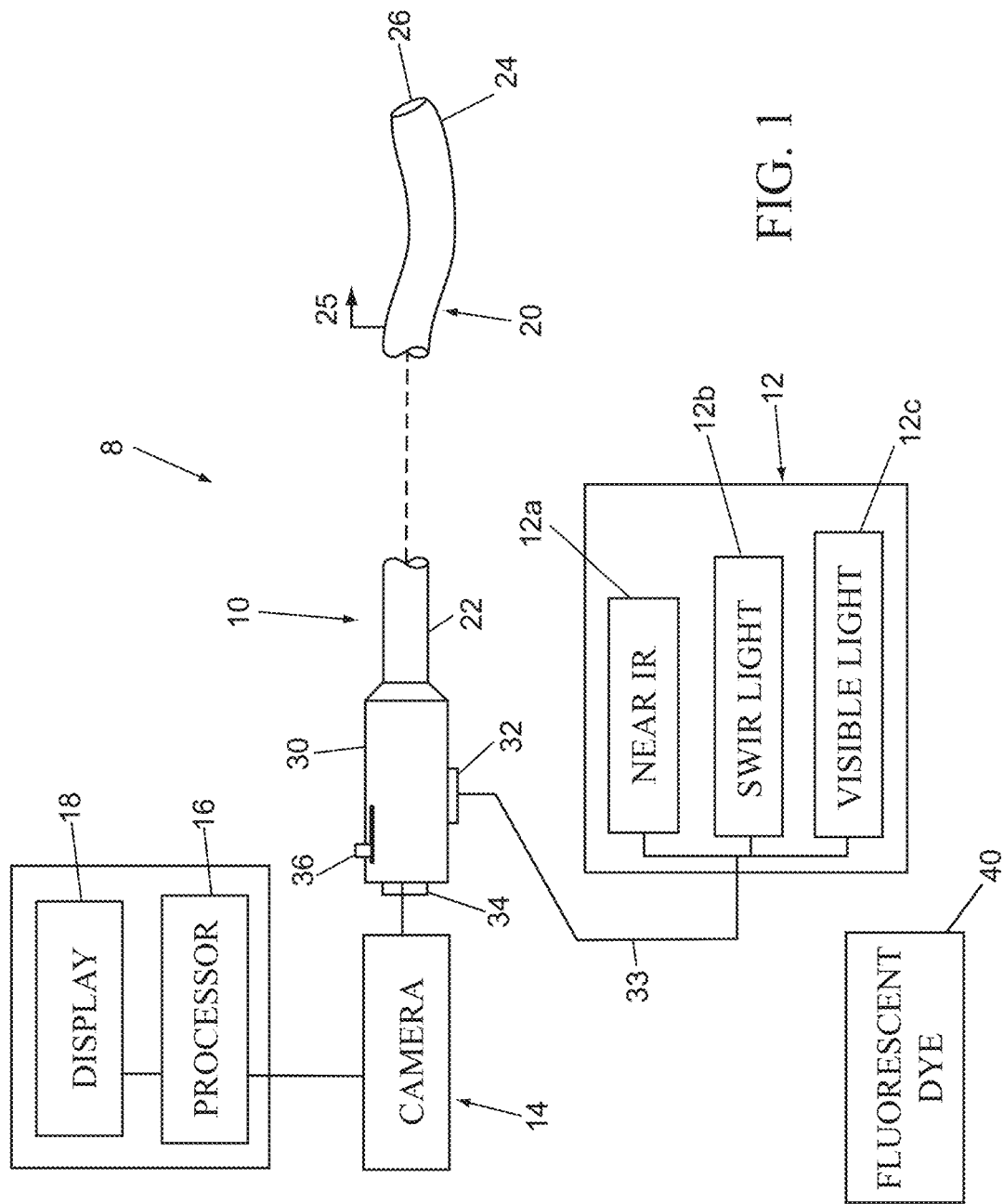
FIG. 1 shows an exemplary embodiment of a system for detecting CSF leaks including an endoscope, a light source, and a camera.

Turning to the drawings, FIG. 1 shows an exemplary embodiment of an apparatus or system 8 for detecting CSF leaks. Generally, the system may be sensitive in the shortwave infrared region, which allows exploration of different areas of the skull base for CSF leaks, as described further elsewhere herein.

As shown in FIG. 1, the system 8 includes an imaging device, e.g., an endoscope 10, a light source 12, e.g., and a camera 14. Optionally, the system 8 may include one or more additional components, e.g., a processor 16 coupled to the camera 14 for processing images from the camera 14 and/or a display 18 coupled to the processor 16 for presenting images to the user, and a source of fluorescent dye, as described further elsewhere herein.

Generally, the endoscope 10 is an endoscope shaft or elongate member 20 including a proximal end 22 including a handle or hub 30, a distal end 24 sized for introduction into a subject's body, and an imaging element 26 carried by the distal end. The elongate member 20 may include one or more lumens (not shown) extending between the proximal and distal ends 22, 24. For example, a fiber lumen may be provided within which one or more optical fibers, e.g., a multiple fiber bundle or individual fibers, may be received that are coupled to the imaging element 26 for delivering light and/or acquiring images beyond the distal end 24, as described further elsewhere herein. Optionally, an infusion and/or instrument lumen may be provided that extends from a port on the hub 30 to an outlet in the distal end 24 (not shown), e.g., to deliver fluids beyond the distal end 24 and/or introducing one or more instruments through the endoscope 10 during a procedure.

The elongate member 20 may be substantially flexible, semi-rigid, and/or rigid along its length, and may be formed from a variety of materials, including plastic, metal, and/or composite materials, as is well known to those skilled in the art. For example, the elongate member 20 may be substantially flexible along a distal portion 25 terminating at the distal end 24 to facilitate advancement through tortuous anatomy, and/or may be semi-rigid or rigid adjacent the proximal end 12 to enhance pushability and/or torqueability of the endoscope 10 without substantial risk of buckling or kinking.

Optionally, the endoscope 10 may include one or more wires or other steering elements slidably received within respective steering lumen(s) (not shown) extending from the proximal end 22 to a fixed location within or at the distal end 24 to allow the distal portion 25 to be bent or otherwise steered, e.g., to allow the distal end 14 to be introduced into a subject's body, e.g., via a nasal cavity to access the skull, to perform a surgical or other medical procedure. In this embodiment, an actuator, e.g., a slider or rotating dial (not shown), may be provided on the hub 30 that is coupled to the steering element(s) to manipulate the shape and/or curvature of the distal end 14 during introduction. Alternatively, the distal portion 25 may be sufficiently flexible that the distal portion 25 may be advanced over a guidewire or other rail previously introduced into the subject's body, e.g., via an instrument lumen of the endoscope 10 (not shown).

The hub 30 may also include one or more connectors, e.g., for coupling the light source 12 and/or camera 14 to the endoscope 10. For example, a first connector 32 may be provided on the hub 30 configured to connect to a fiberoptic cable 33 to couple the light source 12 to the optical fiber(s) within the elongate member 20, thereby optically coupling the light source with the imaging element 26. In addition, a second connector 34, e.g., a C-mount and the like, may be provided on the hub 30 configured to optically couple the camera 14. In an exemplary embodiment, the imaging element 26 may include one or more lenses, filters, and the like to facilitate transmission of light from the light source 12 and/or acquisition of images by the camera 14, e.g., to provide a desired field of view beyond the distal end 24.

One or more optical couplings (not shown) may also be provided within the hub 30, e.g., to direct light from the light source 12 distally through the fiber(s) to the imaging element 26 and/or to direct light from the imaging element 26 to the camera 14 to acquire optical image signals beyond the distal end 24. Alternatively, separate fibers may be provided that extend from the first connector 33 to the distal end 24 and from the second connector 34 to the distal end 24 to transmit light and receive image signals in the separate fibers. In another alternative, a camera, e.g., a CMOS, CCD, and the like, may be carried on the distal end 24 and one or more wires or cables (not shown) may extend proximally from the camera to the hub 30 that may be connected to the processor 16 and/or display 18 via an electrical connector on the hub 30.

With continued reference to FIG. 1, the light source 12 may include an LED box including one or more LEDs, laser, or other light sources configured to deliver multiple wavelengths of light via the endoscope, e.g., from the imaging element on the distal end. Alternatively, one or more of the light sources may be carried on the distal end 24 and one or more wires or cables may extend proximally from the distal end to deliver power and/or otherwise activate/deactivate the light source(s).

For example, as shown, the light source 12 may include one or more near IR LEDs or laser sources 12a, e.g., configured to deliver near IR light, e.g., between about 600-825 nm or between about 785-808 nm, to allow excitation of ICG or other fluorescent dye administered to the subject. In addition, the light source 12 may include one or more SWIR LEDs or lasers 12b, e.g., configured to deliver SWIR light, e.g., between about 1200-2500 nm, or between about 1200-1550 nm, between about 1550-1800 nm, or between about 1800-2500 nm. The SWIR light source 12b may be configured to transmit a narrow band or broadband of light within the SWIR range. If the light source 12b transmits broadband SWIR light, a filter may be provided to narrow the wavelength of light received by the camera 14, as described further elsewhere herein. Examples of SWIR devices that may be included in the apparatus and systems herein are disclosed in U.S. Pat. No. 9,986,915, the entire disclosure of which is expressly incorporated by reference herein.

Optionally, the light source 12 may also include an LED or other white light source 12c configured to deliver visible light, e.g., to allow for surgical navigation when manipulating the endoscope 10 within the subject's body.

The hub 30 may include one or more actuators, e.g., switch 36, that may be actuated to turn desired light sources off and on. For example, a single switch 36 may be provided on the hub 30 that may be moved between a first/off position where the light source 12 is completely off or isolated from the fiber(s) within the elongate member 20, a second position where the near IR and SWIR light sources 12a, 12b are simultaneously activated (without activating the visible light source 12C), and a third position where the visible light source 12c is activated (with the near IR and/or SWIR light sources 12a, 12b remaining on or turning off). For example, the switch 36 may be used to alternate between activating the infrared light sources and the visible light source. Alternatively, separate switches or other actuators may be provided to selectively activate the light sources, e.g., on the hub 30, on a floor step-on switch (not shown) coupled to the hub 30, on the light source 12 itself, and the like.

The camera 14 may include a detector, e.g., a CMOS, CCD, InGas, or other sensor, configured to acquire images within the SWIR bandwidth that may be coupled to the hub 30 via the second connector 34, e.g., a C-mount, to acquire images from the imaging element 26 on the distal end 24 of the endoscope 10. Optionally, the camera 14 may include one or more filters, or separate filters may be coupled between the camera 14 and the second connector 34, to limit the SWIR light received by the camera 14 to a desired narrow band, and the like. For example, the endoscope 10 may include a C-mount adapter on the proximal end that includes SWIR optics and is configured to allow a user to change filters, e.g., within the SWIR region. In addition or alternatively, one or more filters may be provided at the tip of the endoscope, e.g., part of the imaging element 26.

The camera 14 may be connected to a processor 16 and/or display 18, e.g., within a control box, such that signals from the camera 14 may be processed by the processor 16 for presentation on the display 18. Optionally, if desired, the light source 12 may also be provided within the control box to provide a single component to which the endoscope 10 may be connected to use the system 8. Alternatively, the camera may also be provided within the control box. For example, in this alternative, a single connector may be provided on the hub 30 of the endoscope 10 that be connected to a corresponding connector on the control box to allow light to be delivered to the imaging element 26 from the light source(s) within the control box and to deliver image signals to be conveyed from the imaging element 26 to the camera within the control box (or electrical signals from a camera carried on the distal end 24 to the processor).

Figure 2:
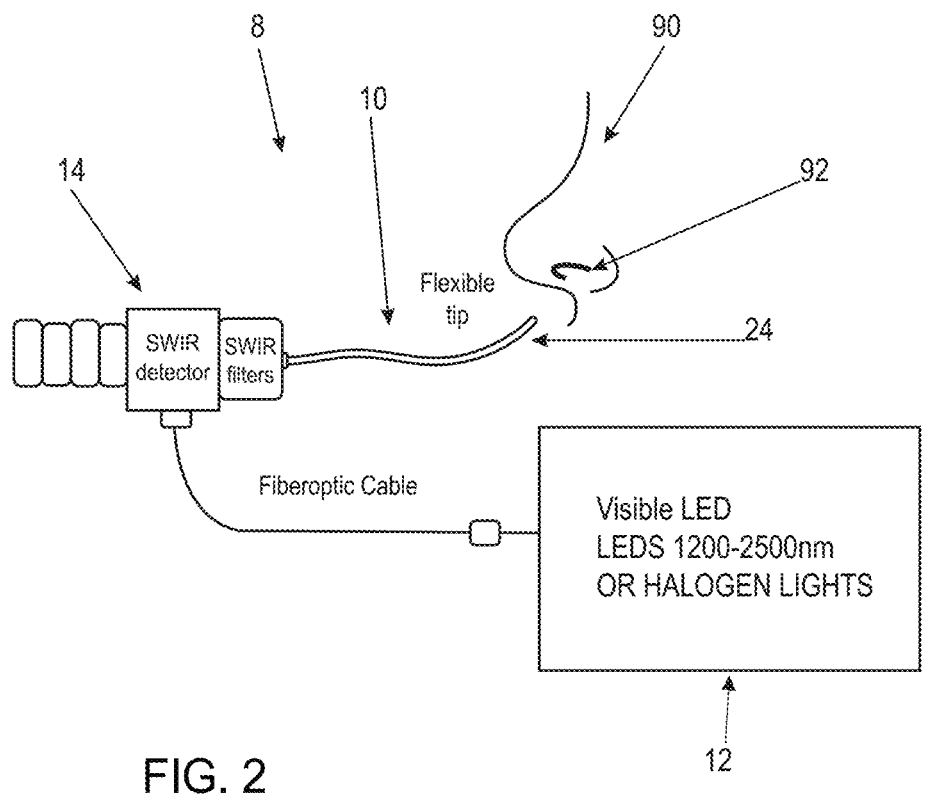
FIG. 2 shows the endoscope of FIG. 1 being introduced into a subject's sinus to acquire images within the subject's skull to detect CSF leaks.
Figure 5:
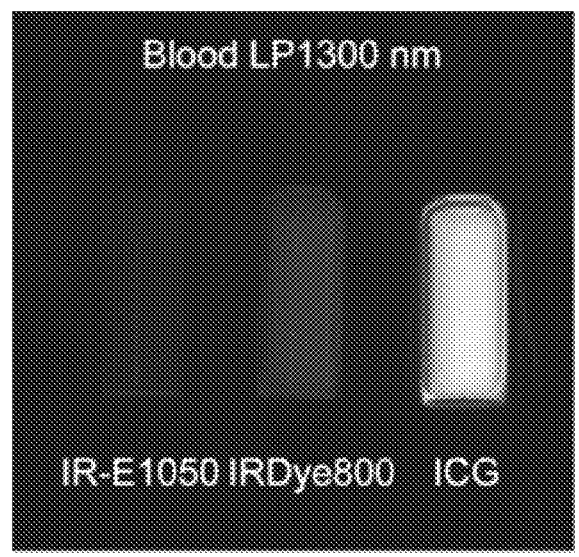
FIG. 5 shows fluorescence of ICG in blood excited at 808 nm.

With additional reference to FIG. 2, the system 8 may be used during or after a medical procedure, e.g., during a surgical procedure within a subject's skull 90, to identify CSF leaks, e.g., such that any leaks that occurred due to the procedure may be sealed before completing the procedure. For example, initially, fluorescent dye, e.g., indocyanine green (ICG) dye, may be administered to the subject in a desired manner, e.g., orally, intravenously, injected locally using a needle introduced through the endoscope 10, or infused through the endoscope (not shown), which may be absorbed by the subject's tissue to cause the tissue to fluoresce when exposed to a predetermined band of infrared light, e.g., as shown in FIG. 5.

As shown in FIG. 2, the distal end 24 of the endoscope 10 may be introduced via the subject's sinus 92 and advanced to a target location, e.g., a surgical site within the subject's skull 90. Optionally, if the light source 12 includes visible light source 12c, the visible light source 12c may be activated and images acquired to facilitate manipulation of the distal end 24 into the target location. Thus, images presented on display 18 may facilitate introduction of the distal end 24, e.g., while using one or more steering elements in the endoscope 10 to navigate the distal end 24 and/or advancing the distal end 24 over a guidewire (not shown) to the target location.

Figure 4:
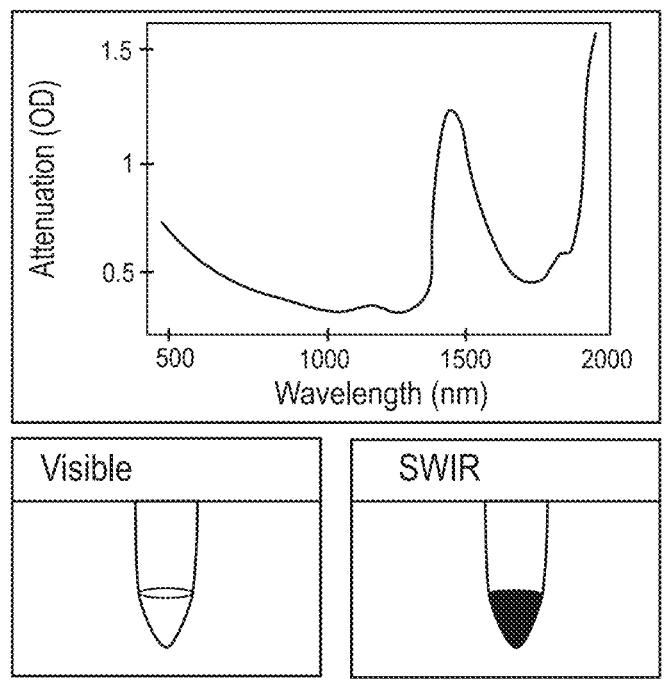
FIG. 4 is a graph showing increased contrast of CSF in the SWIR range due to increased water absorption in the SWIR range.

Once the distal end 24 is positioned as desired within the target location, the visible light source may be deactivated, and the near IR and SWIR light sources 12a, 12b may be activated simultaneously, e.g., using the one or more actuators on the hub 30, LED box 12, or elsewhere for selectively activating and deactivating the light sources. For example, to identify a CSF leak, the near IR and SWIR light sources 12a, 12b may be activated simultaneously to excite the ICG (absorbed by blood and therefore tissues within the subject's body) and to distinguish any CSF present. Because CSF is 99% water having a large absorption in the SWIR band around 1200-1550 nm and above 1800 nm, e.g., as shown in FIG. 4, resulting images acquired by the camera 14 may readily show the contrast between the CSF and surrounding tissue. For example, in a bloody field, the, ICG may create contrast between the CSF and blood. Alternatively, in a clean field of view without substantial blood (or after flushing and/or aspirating blood from the field), SWIR light alone (within the range of about 1200-1700 nm) may provide sufficient contrast to allow the CSF to be presented on images acquired by the camera 14.

Figures 3A, 3B:
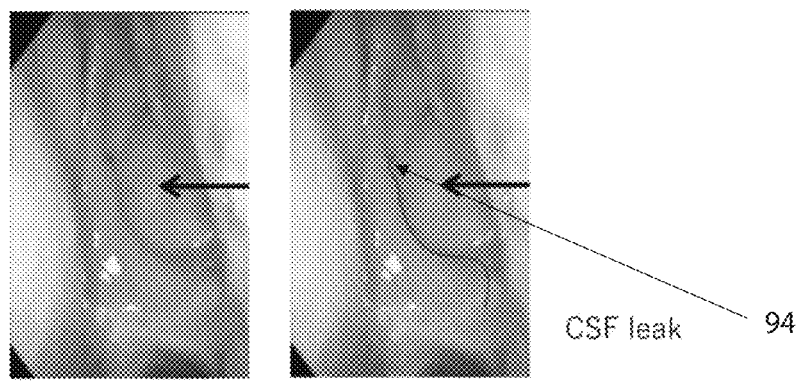
FIGS. 3A and 3B show representative images using fluorescent imaging to identify a CSF leak.

Thus, as represented by the images in FIGS. 3A and 3B, visible light images (FIG. 3A) may provide no indication of a CSF leak, while SWIR images (FIG. 3B) may readily identify a leak 94 given the contrast between the CSF (black since it readily absorbs SWIR light) and the surrounding tissue, which is fluorescing due the absorption of ICG. At any time, the user may activate the white light source 12c (and optionally turn off the IR light sources 12a, 12b) to facilitate directing the distal end 24 of the endoscope 10 within the subject's body and/or to observe one or more instruments introduced via the endoscope 10 to perform a surgical or other procedure. The resulting system and method should be an effective means of diagnosis without the need for intrathecal fluorescein.

Although the systems and methods are described for particular use in detecting CSF leaks within a subject's skull, the systems and methods may also be used for imaging other regions, e.g., for verifying viability of nasal pedicle flaps, or for identifying ureters during laparoscopic robotic surgeries, or leaks in gastrointestinal surgery.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for detecting leakage of cerebrospinal fluid in a subject's body, comprising:
   an imaging device comprising a proximal end, a distal end sized for introduction into the body, and an imaging element carried by the distal end;
   a light source coupled to the imaging device to simultaneously deliver near infrared (IR) light to excite fluorescent dye administered to the body to cause the dye to fluoresce and deliver short wavelength infrared (SWIR) light;
   a camera configured for acquiring images via the imaging element within the SWIR band to facilitate identifying a leak of cerebrospinal fluid; and
   a display coupled to the camera to present the images acquired by the camera to facilitate identifying a leak of cerebrospinal fluid based on contrast between the cerebrospinal fluid and the fluorescent dye absorbed by surrounding tissue or blood which is fluorescing within the SWIR band due to absorption of the fluorescent dye.

2. The apparatus of claim 1, wherein the light source comprises a near IR light source configured to generate the near IR light to the imaging element at a frequency between about 785-808 nm.

3. The apparatus of claim 2, wherein the light source further comprises a SWIR light source configured to generate the SWIR light to the imaging element at a frequency between about 1200-2500 nm.

4. The apparatus of claim 3, wherein the SWIR light source comprises one or more light emitting diodes (LEDs), lasers, or halogen lights.

5. The apparatus of claim 3, wherein the camera is optically coupled to the imaging element for receiving optical signals from the imaging element, the apparatus further comprising a filter for filtering the optical signals such that the camera receives a predetermined narrow band of SWIR light.

6. The apparatus of claim 2, wherein the light source further comprises a visible light source configured to selectively generate visible light to facilitate navigation of the distal end within the body.

7. The apparatus of claim 6, wherein the visible light source is configured to generate white light.

8. The apparatus of claim 6, further comprising one or more actuators coupled to the light source for simultaneously activating the near IR light source and a SWIR light source while the visible light source is deactivated.

9. The apparatus of claim 8, wherein the one or more actuators are configured to activate the visible light source such that the camera acquires visible light images to facilitate navigation of the distal end within the body.

10. The apparatus of claim 9, wherein the one or more actuators are configured to activate the visible light source while the near IR and SWIR light sources are deactivated.

11. The apparatus of claim 1, further comprising a processor coupled to the camera and the display for processing electrical signals from the camera corresponding to the images acquired by the imaging element to present the images on the display.

12. A system for detecting leakage of cerebrospinal fluid in a subject's body, comprising:
    an imaging device comprising a proximal end, a distal end sized for introduction into the body, and an imaging element carried by the distal end;
    a light source coupled to the imaging device to simultaneously deliver near infrared (IR) light to excite fluorescent dye administered to the body to cause the dye to fluoresce and deliver short wavelength infrared (SWIR) light;
    a camera configured for acquiring images via the imaging element within the SWIR band to facilitate identifying a leak of cerebrospinal fluid;
    a source of fluorescent dye for administration to the subject configured to fluoresce within the SWIR band when exposed to the near IR light; and
    a display coupled to the camera to present the images acquired by the camera to facilitate identifying a leak of cerebrospinal fluid based on the contrast in the images between the cerebrospinal fluid and the fluorescent dye absorbed by surrounding tissue or blood which is fluorescing within the SWIR band due to absorption of the fluorescent dye.

13. The system of claim 12, wherein the source of fluorescent dye comprises a container of indocyanine green (ICG) dye.

14. The system of claim 13, further comprising a processor coupled to the camera and the display for processing electrical signals from the camera corresponding to the images acquired by the imaging element to present the images on the display.

15. The system of claim 12, wherein the light source comprises a near IR light source configured to generate the near IR light to the imaging element at a frequency between about 785-808 nm.

16. The system of claim 15, wherein the light source further comprises a SWIR light source configured to generate the SWIR light to the imaging element at a frequency between about 1200-2500 nm.

17. The system of claim 16, wherein the light source further comprises a visible light source configured to selectively generate visible light to facilitate navigation of the distal end within the body, the system further comprising one or more actuators coupled to the light source for either a) simultaneously activating the near IR light source and the SWIR light source while the visible light source is deactivated such that SWIR images are presented on the display, or b) activating the visible light source while the near IR and SWIR light sources are deactivated such that visible light images are presented on the display to facilitate navigation of the distal end within the body.

18. The system of claim 12, wherein the camera is optically coupled to the imaging element for receiving optical signals from the imaging element, the system further comprising a filter for filtering the optical signals such that the camera receives a predetermined narrow band of SWIR light.

19. A method for detecting leakage of cerebrospinal fluid in a subject's body, comprising:

administering fluorescent dye to the body;
introducing an imaging device into a target location within the body;
delivering near infrared (IR) light via the imaging device to excite the fluorescent dye to cause the dye to fluoresce within the shortwave infrared (SWIR) band; and
acquiring images via the imaging device at a frequency between about 1200-2500 nm to identify a leak of cerebrospinal fluid within the target location based on contrast between the cerebrospinal fluid and the fluorescent dye absorbed by surrounding tissue or blood which is fluorescing within the SWIR band due to absorption of the fluorescent dye.

20. The method of claim 19, wherein introducing the imaging device into a target location comprises introducing the imaging device into the subject's sinus to acquire images within the subject's skull to detect the leakage of the cerebrospinal fluid.

* * * * *